United States Patent [19]

Manoury et al.

[11] Patent Number: 4,806,560
[45] Date of Patent: Feb. 21, 1989

[54] IMIDAZO[4,5-B]PYRIDIN-2-ONE DERIVATIVES

[75] Inventors: Philippe Manoury, Verrieres le Buisson; Jean Binet, Breuillet; Elisabeth Dewitte, St. Gratien, all of France

[73] Assignee: Synthelabo, France

[21] Appl. No.: 105,243

[22] Filed: Oct. 7, 1987

[30] Foreign Application Priority Data

Oct. 8, 1986 [FR] France .................. 86 13995

[51] Int. Cl.$^4$ .......................... C07D 471/04
[52] U.S. Cl. ................................ 546/118
[58] Field of Search ........................ 546/118

[56] References Cited

FOREIGN PATENT DOCUMENTS 092391 10/1983 European Pat. Off. .
098499 1/1984 European Pat. Off. .

Primary Examiner—Mary C. Lee
Assistant Examiner—Bernard I. Dentz
Attorney, Agent, or Firm—Wegner & Bretschneider

[57] ABSTRACT

Imidazo[4,5-b]pyridin-2-one derivatives of the formula (I)

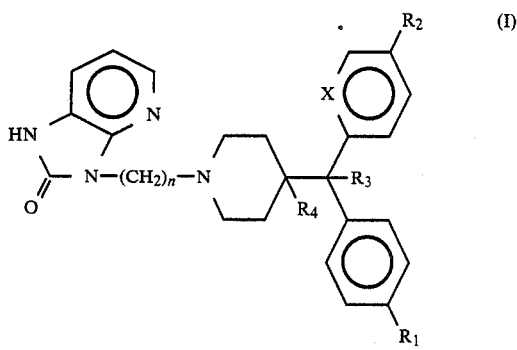

in which n is 2, 3 or 4, x is =CH— or =N—, $R_1$ and $R_2$, which may be the same or different, each represent hydrogen, halogen or $(C_{1-4})$ alkoxy and either $R_3$ is H or OH and $R_4$ is H, or $R_3$ and $R_4$ together form a direct bond, their enantiomers and their addition salts with pharmaceutically acceptable acids are pharmacologically active, for example as antagonists to histamine and serotonin.

2 Claims, No Drawings

IMIDAZO[4,5-B]PYRIDIN-2-ONE DERIVATIVES

The present invention relates to imidazo[4,5-b]pyridin-2-one derivatives, to their preparation and to pharmaceutical compositions containing them.

The invention provides a compound which is an imidazo[4,5-b]pyridin-2-one derivative of formula (I)

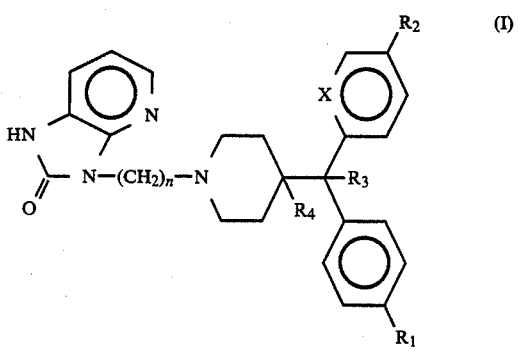

wherein n is 2, 3 or 4, X is =CH— or =N—, $R_1$ and $R_2$, which may be the same or different, each represent hydrogen, halogen or $(C_{1-4})$alkoxy and either $R_3$ is hydrogen or hydroxy and $R_4$ is hydrogen, or $R_3$ and $R_4$ together form a direct bond, an enantiomer thereof or an addition salt with a pharmaceutically acceptable acid.

The compounds may give rise to enantiomers, for example when $R_1$ is different from $R_2$ or when X is =N—. In such cases, the enantiomers of compounds (I) form part of the invention.

According to the invention, compounds (I) may be prepared according to reaction schemes 1 and 2 given in appendices 1 and 2.

According to the reaction scheme 1, a compound (II) is reacted either with a compound (III) so as to obtain compound (IV) which is reacted with hydrazine in order to obtain compound (VI), or with acrylonitrile or a compound Y—$(CH_2)_{n-1}$—CN, in which Y is a labile group, so as to obtain compound (V) which is hydrogenated, preferably in the presence of Raney nickel, into compound (VI).

The latter is then reacted with 2-chloro-3-nitropyridine, for example in the presence of potassium carbonate, preferably in ethanol, so as to obtain compound (VII) which is hydrogenated into compound (VIII); finally, this compound (VIII) is reacted with ethyl chloroformate or ethyl pyrocarbonate, suitably in toluene, in order to obtain compound (I). Alternatively, the intermediate (VIII) may be reacted with urea, preferably at between 100° and 180° C., or with carbonyldiimidazole.

According to reaction scheme 2, compound (IX) is esterified into compound (X) which is hydrogenated into compound (XI), the latter is reacted with urea so as to obtain compound (XII) which is hydrolysed into the alcohol (XIII), this alcohol is converted into the alcohol derivative (XIV), in which Y is a labile group, and finally, compound (XIV) is reacted with a compound (II) in order to obtain compound (I).

Reaction schemes 1 and 2 are illustrated in the Examples below.

Some of the compounds (II) are described in U.S. Pat. No. 2,804,222 and in the literature by Duncan et al., J. Med. Chem. 13, 1, 1970.

Compounds (II) may be prepared according to reaction scheme 3 given in appendix 3: a compound (XV) is reacted with an organometallic compound (XVI) and the compound obtained (XVII) is then hydrolysed or hydrogenolysed in order to obtain compound (II).

Compounds (I) in which both $R_3$ and $R_4$ are hydrogen may also be obtained by the hydrogenolysis of compounds (I) in which $R_4$ is hydrogen and $R_3$ is hydroxy or by the hydrogenation of compounds (I) in which $R_3$ and $R_4$ together represent a direct bond.

The following Examples illustrate the invention.

The structure of the compounds was confirmed by analyses and IR and NMR spectra.

EXAMPLE 1

3-{2-[4-(Hydroxydiphenylmethyl)-1-piperidyl]ethyl}-1,3-dihydro-2H-imidazo[4,5-b]pyridin-2-one

1.1.

2-{2-[4-(Hydroxydiphenylmethyl)-1-piperidyl]ethyl}-1H-isoindole-1,3-dione

A mixture of 15 g (0.056 mol) of α,α-diphenyl-4-piperidinemethanol, 14.5 g (0.056 mol) of 2-(2-bromoethyl)-1H-isoindole-1,3-dione and 6.7 g (0.063 mol) of sodium carbonate in 150 ml of methyl isobutyl ketone is heated at reflux temperature for 5 hours.

After evaporating off the solvent, the residue is taken up with water and chloroform. The organic phase is washed with water, dried, filtered and evaporated. An oil is obtained, which crystallizes after purification on silica column. A product melting at 166°–169° C. is obtained.

1.2.

1-(2-Aminoethyl)-α,α-diphenyl-4-piperidinemethanol

A solution of 11.7 g (0.026 mol) of the above derivative in 200 ml of methanol containing 1.3 ml of hydrazine is stirred for 12 h at ambient temperature. The solution is evaporated to dryness, the residue is taken up with water and acidified with hydrochloric acid. The insolubles are filtered and extracted with methylene chloride.

The aqueous phase is made alkaline, and extracted with methylene chloride. The organic phase is washed with water, dried, filtered and evaporated.

The product, which is white, melting at 164°–166° C. is obtained.

1.3.

1-{-2-[(3-Nitro-2-pyridyl)amino]ethyl}-α,α-diphenyl-4-piperidinemethanol 11.9 g (0.04 mol) of the above product is refluxed for 12 h with 6.4 g (0.04 mol) of 2-chloro-3-nitropyridine and 5.8 g (0.042 mol) of potassium carbonate in 200 ml of ethanol.

The mixture is evaporated, and the evaporation residue is taken up with water and ether. The ethereal phase is washed with water, dried, filtered and evaporated.

A yellow oil is obtained, which is used in the crude state in the following stage.

1.4.
1-{2-[(3-amino-2-pyridyl)amino]ethyl}-α,α-diphenyl-4-piperidinemethanol 17.3 g (0.04 mol) of the above nitro derivative dissolved in 150 ml of methanol are hydrogenated at ambient temperature, under a hydrogen pressure of 50 psi, in the presence of 0.5 g of platinum oxide.

When the reaction is complete, the catalyst is filtered off and the filtrate is evaporated.

A highly coloured oil is obtained, which is used in the crude state in the next stage of synthesis.

1.5.
3-{2-[4-(Hydroxydiphenylmethyl)-1-piperidyl]ethyl}-1,3-dihydro-2H-imidazo[4,5-b]pyridin-2-one 16.8 ml (0.114 mol) of ethylpyrocarbonate are introduced with care into a solution of 15.2 g (0.038 mol) of the above oil in 100 ml of toluene. The mixture is stirred for 2 h after the completion of the addition and the toluene is then evaporated off. The black gum thus obtained is solubilized in 100 ml of ethanol; 1 g of sodium is added and the mixture is heated at reflux for 1 h.

The mixture is then evaporated and the residual gum is taken off with water. The solution is neutralized with 2.5 ml of acetic acid and extracted with methylene chloride. The organic phase is washed with water, dried, filtered and evaporated. The product obtained is purified by silica column chromatography. The product is obtained, which is recrystallized in ethyl acetate. m.p.=213°-217° C.

EXAMPLE 2
3-[3-{4-[Hydroxy(4-fluorophenyl)(2-pyridyl)methyl]-1-piperidyl}propyl]-1,3-dihydro-2H-imidazo[4,5-b]pyridin-2-one

2.1.
3-{4-[Hydroxy(4-fluorophenyl)(2-pyridyl)methyl]-1-piperidyl}propanenitrile 2.3 ml (0.035 mol) of acrylonitrile are added dropwise to a solution of 10 g (0.035 mol) of α-(4-fluorophenyl)-α-(2-pyridyl)-4-piperidinemethanol in 60 ml of ethanol and 1 ml of Triton B.

The solution is allowed to stand for 2 days at ambient temperature. The solution is evaporated to dryness and the residual mixture is taken up with water and methylene chloride. The organic phase is washed with water, dried, filtered and evaporated.

The product is obtained in the crystallized form. m.p.=45°-48° C.

2.2.
1-(3-Aminopropyl)-α-(4-fluorophenyl)-α-(2-pyridyl)-4-piperidinemethanol 12.2 g (0.035 mol) of the above nitrile dissolved in 70 ml of ammoniacal ethanol are hydrogenated in an autoclave, under a hydrogen pressure of 60 kg/cm$^2$ at a temperature of 70° C., in the presence of Raney nickel.

When the reaction is complete, the catalyst is filtered off and the filtrate is evaporated. A colourless oil is obtained, which can be used without further purification in the next stage. A sample is converted into oxalate. m.p.=124°-129° C.

2.3.
1-{3-[(3-Nitro-2-pyridyl)amino]propyl}-α-4-fluorophenyl)-α-(2-pyridyl)-4-piperidinemethanol This product is prepared using the method described in paragraph 1.3 starting with 7.6 g (0.022 mol) of the above product and 3.5 g (0.022 mol) of 2-chloro-3-nitropyridine. The product is obtained, which is used in the crude state in the next stage of synthesis.

2.4.
1-{3-[(3-Amino-2-pyridyl)amino]propyl}-α-(4-fluorophenyl)-α-(2-pyridyl)-4-piperidinemethanol.

The method described in paragraph 1.4 is used starting with 5.6 g (0.012 mol) of the above derivative. A strongly coloured oil is obtained, which is used in the crude state in the next stage.

2.5.
3-[3-{4-[Hydroxy(4-fluorophenyl)(2-pyridyl)methyl]-1-piperidyl}propyl]-1,3-dihydro-2H-imidazo[4,5-b]pyridin-2one The product is prepared using the same method as that described in paragraph 1.5, starting with 5.2 g (0.012 mol) of the above product and 7 ml of ethyl pyrocarbonate. The product is obtained, which is recrystallized in ethyl acetate. m.p.=140°-144° C.

EXAMPLE 3
3-{1-[4-(Hydroxydiphenylmethyl)-1-piperidyl]-3-propyl}-1,3-dihydro-2H-imidazo[4,5-b]pyridin-2-one 3.1. 3-[(3-Nitro-2-pyridyl)amino]-1-propyl benzoate 70 ml of benzoyl chloride are introduced dropwise into a solution of 77.8 g (0.04 mol) of 3-[(3-nitro-2-pyridyl)amino]propanol (M. ISRAEL, N. TIROSH, J. Med. Chem. 1973, 16, 520) in 48.5 ml of pyridine and 800 ml of benzene. The mixture is stirred for 2 h at ambient temperature and the precipitate is filtered. The filtrate is washed with 1N hydrochloric acid and then with water. Drying, filtering and evaporation are carried out. A crystallized product is obtained.

3.2. 3-[(3-Amino-2-pyridyl)amino]-1-propyl benzoate 30 g (0.1 mol) of the above nitro derivative dissolved in 300 ml of methanol is hydrogenated in a Parr bomb, at a hydrogen pressure of 50 psi, at ambient temperature, in the presence of 2 g of platinum oxide.

After usual treatment, the very dark coloured product is obtained, which is used as such as in the next stage.

3.3.
3-(1-Hydroxy-3-propyl)-1,3-dihydro-2H-imidazo[4,5-b]pyridin-2-one 27.1 g (0.1 mol) of the above product is heated at reflux temperature, for 24 h, with 24.3 g (0.15 mol) of carbonyldiimidazole dissolved in 150 ml of chloroform. The mixture is cooled, washed with water, and the organic phase is dried, filtered and evaporated. The product obtained is chromatographed on silica column; the product is obtained, which is recrystallized in a mixture of isopropyl ether and ethyl acetate. m.p.=145°-148° C.

3.4.
3-(1-Hydroxy-3-propyl)-1,3-dihydro-2H-imidazo[4,5-b]pyridin-2-one 18.2 g (0.061 mol) of the above ester is hydrolysed, at 50°-60° C., in 300 ml of 85% methanol and 8.5 g of potassium hydroxide pellets. When the reaction is complete, the mixture is evaporated and the residue is extracted with methyl ethyl ketone under reflux. The solvent is evaporated off and the product is obtained, which is recrystallized in methyl ethyl ketone. (m.p.=160°-163° C.)

The hydrochloride is prepared in methanol by adding ethereal hydrogen chloride. m.p.=186°-190° C.

3.5.
3-(1-Chloro-3-propyl)-1,3-dihydro-2H-imidazo[4,5-b]pyridin-2-one hydrochloride A suspension of 5 g (0.021 mol) of the above product in the hydrochloride form in 100 ml of thionyl chloride and 0.3 ml of DMF is heated under reflux for 4 h.

The excess thionyl chloride is evaporated off and the residual oil is taken up with acetone. The product is obtained in a solid form.

3.6.
3-{1-[4-(Hydroxydiphenylmethyl)-1-piperidyl]-3-propyl}-1,3-dihydro-2H-imidazo[4,5-b]pyridin-2-one 1.05 g (0.005 mol) of the above product, 1.3 g (0.005 mol) of α,α-diphenyl-4-piperidinemethanol and 1 g of sodium bicarbonate in 50 ml of ethanol are heated under reflux for 5 h.

The inorganic products are filtered and the filtrate is evaporated. The residue is solubilized in chloroform, the organic phase is washed with 1N sodium hydroxide and then with water. Washing, filtering and evaporation are carried out. The product is purified by silica column chromatography. The product is obtained, which is recrystallized in methyl ethyl ketone. m.p.=190°-192° C.

EXAMPLE 4
3-[3-{4-[Bis(4-fluorophenyl)methylene]-1-piperidyl}propyl]-1,3-dihydro-2H-imidazo[4,5-b]pyridin-2-one

4.1.
3-(3-Aminopropyl)-α,α-bis(4-fluorophenyl)-4-piperidinemethanol

This product is prepared as described in Example 2.2. starting with 18.2 g of 3-{4-[bis(4-fluorophenyl)hydroxymethyl]-1-piperidyl}propanenitrile.

4.2.
3-[3-{4-[Bis(4-fluorophenyl)hydroxymethyl]-1-piperidyl}propyl]-1,3-dihydro-2H-imidazo[4,5-b]pyridin-2-one This product is synthesized starting with the product obtained in 4.1. according to the method described in Example 2 (2.3. to 2.5.). m.p.=183°-185° C.

4.3.
1 g of 3-[3-{4-[bis(4-fluorophenyl)hydroxymethyl]-1-piperidyl}propyl]-1,3-dihydro-2H-imidazo[4,5-b]pyridin-2-one dissolved in 50 ml of 6N hydrochloric acid is heated under reflux for 2 h.

The reaction mixture is made alkaline and extracted with methylene chloride. After usual treatment, a product is obtained, which is purified by silica column chromatography. The product is obtained in the crystallized form. m.p.=163°-165° C.

TABLE

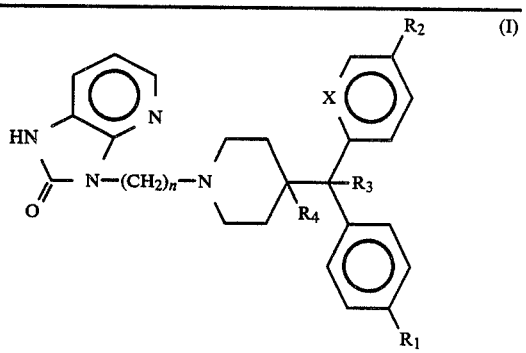

| Compound | n | X | $R_1$ | $R_2$ | $R_3$ | $R_4$ | m.p. (°C.) |
|---|---|---|---|---|---|---|---|
| 1 | 2 | CH | H | H | OH | H | 213-217 |
| 2 | 2 | CH | H | H | H | H | 228-229 |
| 3 | 3 | CH | H | H | OH | H | 190-192 |
| 4 | 3 | CH | F | F | OH | H | 183-185 |
| 5 | 3 | CH | F | F | bond | | 163-165 |
| 6 | 3 | CH | F | H | OH | H | 182-188 |
| 7 | 3 | CH | Cl | F | OH | H | 138 |
| 8 | 3 | CH | OCH$_3$ | F | OH | H | 161-164 |
| 9 | 3 | N | F | H | OH | H | 140-144 |
| 10 | 4 | N | F | H | OH | H | 155 |

The compounds were subjected to various pharmacological tests showing their antagonistic activity towards histamine and serotonin.

In vivo activity: histamine- or serotonin-induced inflammation.

The intraplantar injection into one of the hind paws of rat, of histamine (200 μg) or of serotonin (1 μg), causes an oedema, which is measured 1 h after injection using a Ugo Basile mercury plethysmometer.

The compounds of the invention suspended in a 1% solution of Tween in distilled water, are administered p.o. (0.5 ml/100 g) 1 h before injecting the inflammatory agent.

The AD$_{40}$ values (dose which decreases the volume of oedema by 40%) are determined.

The compounds of the invention have an AD$_{40}$ ranging from 0.5 to 5 mg/kg when the inflammatory agent is histamine.

Some compounds of the invention are active at an AD$_{40}$ ranging from 0.2 to 2 mg/kg when the inflammatory agent is serotonin.

Therefore, the compounds of the invention may be used as antiallergics, antipruritics for the treatment of respiratory allergies such as rhinitis, hay fever, skin allergies such as dermatites, rashes, eye allergies, Quincke's oedema and various allergic symptoms and for the treatment of asthma.

The derivatives of the invention which are more specifically active as serotonin-antagonists may be used for combating some undesirable effects of this mediator at the peripheral level or at the central level. They are particularly intended for the treatment of migraine.

Consequently, the invention comprises all pharmaceutical compositions containing the compounds and-/or their salts as active principles, in combination with any excipient suitable for their administration, in particular by the oral or the parenteral route.

Their routes of administration may be the oral and the parenteral routes.

The daily dose may range from 5 to 200 mg.

Appendix 1
Scheme 1
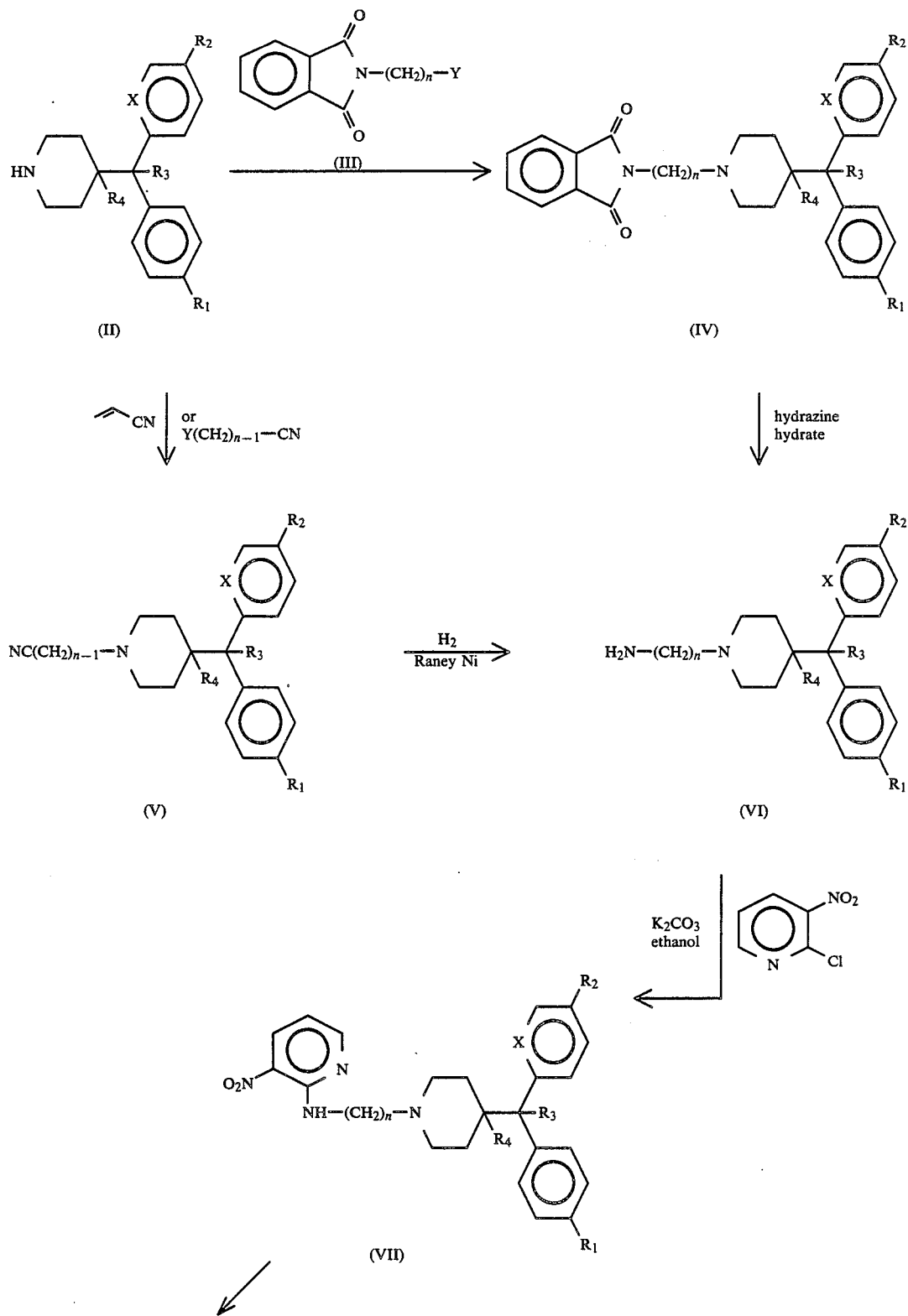

Appendix 1-continued
Scheme 1
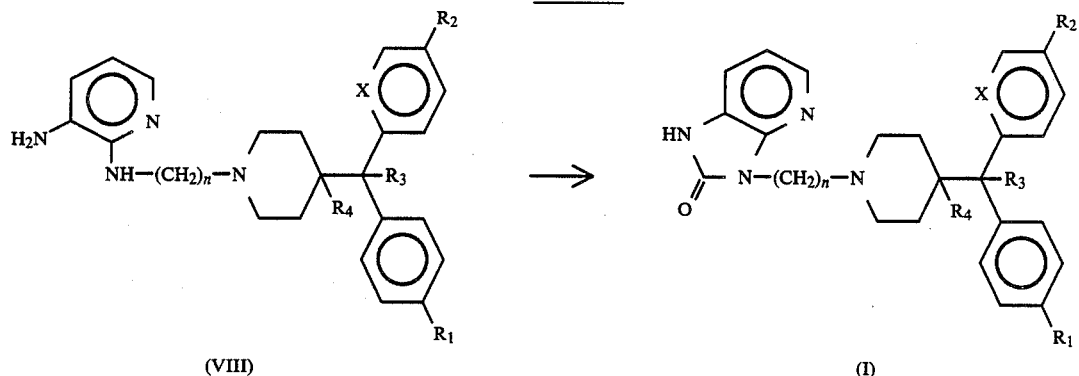
Appendix 2
Scheme 2
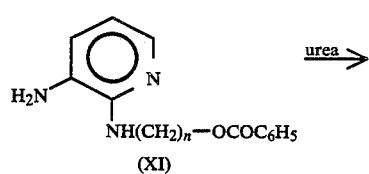
(IX)
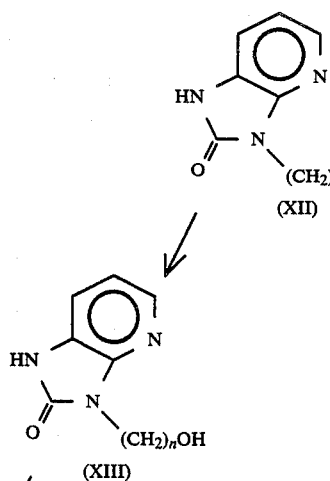
Appendix 2-continued
Scheme 2
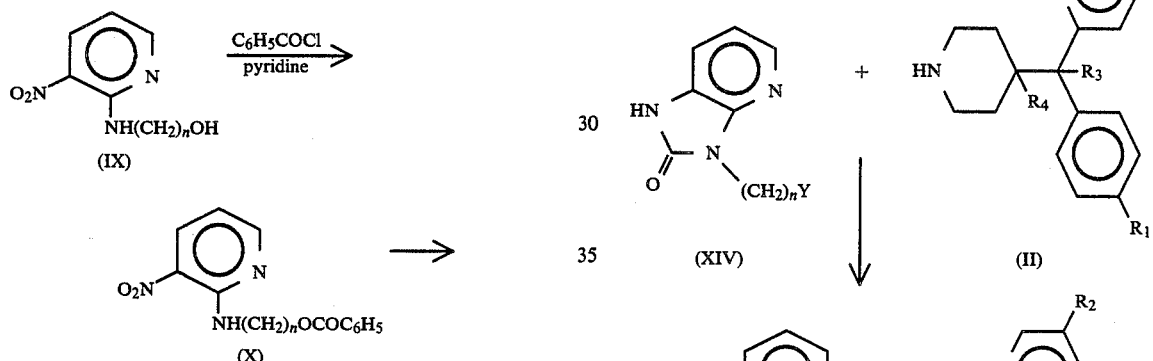
Appendix 3
Scheme 3
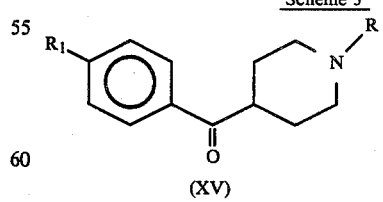
(XV)
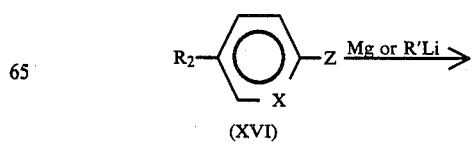
(XVI)

Appendix 3-continued

Scheme 3

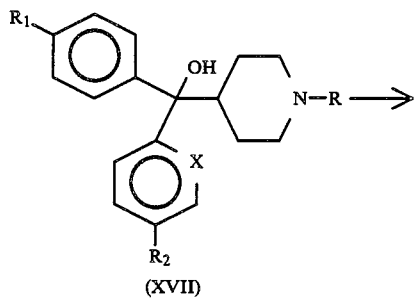

(XVII)

Appendix 3-continued

Scheme 3

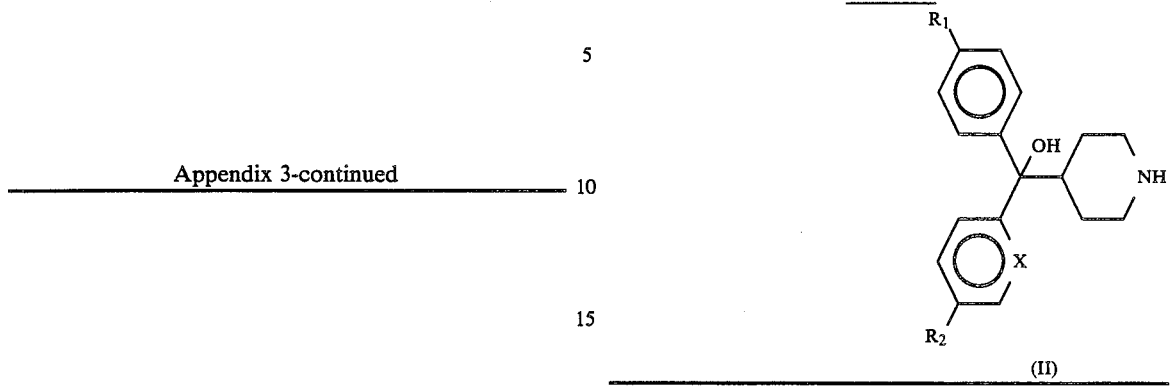

(II)

We claim:

1. A compound which is an imidazo[4,5-b]pyridin-2-one derivative of formula (I)

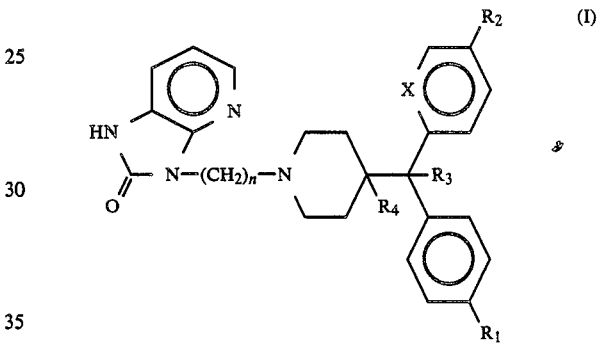

wherein n is 2, 3 or 4, X is =CH— or =N—, $R_1$ and $R_2$, which may be the same or different, each represent hydrogen, halogen or $(C_{1-4})$alkoxy and either $R_3$ is hydrogen or hydroxy and $R_4$ is hydrogen, or $R_3$ and $R_4$ together form a direct bond, an enantiomer thereof or an addition salt with a pharmaceutically acceptable acid.

2. A compound according to claim 1 wherein $R_1$ is hydrogen, chlorine, fluorine or methoxy, and $R_2$ is hydrogen or fluorine.

* * * * *